(12) United States Patent
Ninomiya et al.

(10) Patent No.: US 9,451,931 B2
(45) Date of Patent: Sep. 27, 2016

(54) CARRIAGE FOR ULTRASONIC DIAGNOSIS DEVICE

(71) Applicant: HITACHI ALOKA MEDICAL, LTD., Tokyo (JP)

(72) Inventors: Atsushi Ninomiya, Tokyo (JP); Kazuyuki Yanase, Tokyo (JP); Masaru Yokoyama, Tokyo (JP); Tsuneo Kasanami, Tokyo (JP); Katsumi Usami, Tokyo (JP)

(73) Assignee: HITACHI ALOKA MEDICAL, LTD., Tokyo (JP)

( * ) Notice: Subject to any disclaimer, the term of this patent is extended or adjusted under 35 U.S.C. 154(b) by 0 days.

(21) Appl. No.: 14/381,269

(22) PCT Filed: Jan. 24, 2013

(86) PCT No.: PCT/JP2013/051450
§ 371 (c)(1),
(2) Date: Aug. 27, 2014

(87) PCT Pub. No.: WO2013/145826
PCT Pub. Date: Oct. 3, 2013

(65) Prior Publication Data
US 2015/0105660 A1 Apr. 16, 2015

(30) Foreign Application Priority Data
Mar. 29, 2012 (JP) ................. 2012-076403

(51) Int. Cl.
*B62B 3/02* (2006.01)
*A61B 8/00* (2006.01)
(Continued)

(52) U.S. Cl.
CPC ........... *A61B 8/4405* (2013.01); *A61B 8/4411* (2013.01); *A61B 8/4427* (2013.01);
(Continued)

(58) Field of Classification Search
CPC ....... B62B 3/02; B62B 3/10; B62B 2202/06; B62B 2202/56; B62B 2202/48; A47B 21/0314; A61B 8/4405
See application file for complete search history.

(56) References Cited

U.S. PATENT DOCUMENTS 6,394,402 B2 * 5/2002 Coonan .................. A47B 21/00
248/123.11
7,594,668 B2 * 9/2009 Arceta et al. .............. 280/47.35
(Continued)

FOREIGN PATENT DOCUMENTS

| JP | 6-85863 A | 3/1994 |
|---|---|---|
| JP | 2002-542870 A | 12/2002 |

(Continued)

OTHER PUBLICATIONS

International Preliminary Report for PCT/JP2013/051450, dated Oct. 9, 2014.
(Continued)

*Primary Examiner* — Emma K Frick
(74) *Attorney, Agent, or Firm* — Baker Botts L.L.P.

(57) ABSTRACT

The present invention provides a cart for an ultrasonic diagnostic apparatus, having a high degree of flexibility in moving a top board on which the ultrasonic diagnostic apparatus is placed, and enabling a stable operation wherever the top board is moved. In the cart for the ultrasonic diagnostic apparatus, a vertical movement mechanism 60 is fixed on a base. A movable part 62 of the vertical movement mechanism is provided with a swing mechanism 70 that swings in the up-and-down direction, enabling up-and-down movement of the top board 10 according to both the vertical movement mechanism and the swing mechanism. The position of the movable part with which the swing mechanism is coupled is displaced forward from the vertical central axis of the vertical movement mechanism. The top board for placing the ultrasonic diagnostic apparatus is coupled with the swinging end of the swing mechanism, via a mechanism 80 for horizontal movement and/or a mechanism 90 for rotating the top board.

9 Claims, 10 Drawing Sheets

(51) Int. Cl.
*F16M 11/08* (2006.01)
*F16M 11/18* (2006.01)
*F16M 11/20* (2006.01)
*F16M 11/24* (2006.01)
*F16M 11/42* (2006.01)
*G01S 15/89* (2006.01)
*G01S 7/52* (2006.01)

(52) U.S. Cl.
CPC .............. *B62B 3/02* (2013.01); *F16M 11/08* (2013.01); *F16M 11/18* (2013.01); *F16M 11/2021* (2013.01); *F16M 11/2085* (2013.01); *F16M 11/2092* (2013.01); *F16M 11/24* (2013.01); *F16M 11/42* (2013.01); *A61B 8/4433* (2013.01); *B62B 2202/56* (2013.01); *B62B 2206/06* (2013.01); *G01S 7/52079* (2013.01); *G01S 15/899* (2013.01)

(56) References Cited

U.S. PATENT DOCUMENTS

| | | | |
|---|---|---|---|
| 8,109,527 B2 * | 2/2012 | Bustle et al. .............. | 280/47.35 |
| 8,240,684 B2 * | 8/2012 | Ross et al. ................. | 280/47.34 |
| 8,286,977 B2 * | 10/2012 | Butler et al. ............... | 280/47.35 |
| 8,333,698 B2 * | 12/2012 | Ninomiya ................ | A61B 8/00 600/407 |
| 8,714,569 B2 * | 5/2014 | Lu et al. ......................... | 280/35 |
| 9,039,016 B2 * | 5/2015 | Abernethy ................ | B62B 3/02 280/6.15 |
| 2002/0143256 A1 | 10/2002 | Wing et al. | |
| 2003/0025054 A1 | 2/2003 | Toennesland et al. | |
| 2004/0152982 A1 | 8/2004 | Hwang et al. | |
| 2005/0288571 A1 | 12/2005 | Perkins et al. | |
| 2007/0012841 A1 * | 1/2007 | Chen .......................... | 248/298.1 |
| 2008/0252045 A1 * | 10/2008 | Rossini et al. ................ | 280/659 |
| 2009/0315287 A1 * | 12/2009 | Rossini ..................... | 280/47.35 |
| 2010/0094130 A1 * | 4/2010 | Ninomiya et al. ............ | 600/437 |
| 2010/0213679 A1 * | 8/2010 | Smith et al. ............... | 280/47.35 |
| 2011/0201927 A1 | 8/2011 | Hayakawa et al. | |
| 2011/0224544 A1 | 9/2011 | Ahn et al. | |
| 2013/0197364 A1 * | 8/2013 | Han ...................... | A61B 8/4405 600/440 |
| 2013/0200579 A1 * | 8/2013 | Abernethy et al. .......... | 280/6.15 |
| 2013/0307237 A1 * | 11/2013 | Chen ............................. | 280/35 |
| 2014/0117635 A1 * | 5/2014 | Ninomiya ............ | A61B 8/4405 280/35 |
| 2014/0138925 A1 * | 5/2014 | Ono ......................... | B62B 3/02 280/35 |
| 2015/0342562 A1 * | 12/2015 | Messina ............... | A61B 8/4405 248/544 |
| 2015/0351719 A1 * | 12/2015 | Ninomiya ................ | B62B 3/10 348/163 |
| 2016/0066884 A1 * | 3/2016 | Shin ..................... | A61B 8/4405 600/437 |

FOREIGN PATENT DOCUMENTS

| | | |
|---|---|---|
| JP | 2003-144433 A | 5/2003 |
| JP | 2006-518254 A | 8/2006 |
| JP | 2007-6969 A | 1/2007 |
| JP | 2008-126015 A | 6/2008 |
| JP | 2008-536555 A | 9/2008 |
| JP | 2009-201844 A | 9/2009 |
| JP | 2010-57886 A | 3/2010 |
| JP | 2010-220802 A | 10/2010 |
| JP | 2011-167305 A | 9/2011 |
| WO | WO 2006/111874 A2 | 10/2006 |

OTHER PUBLICATIONS

International Preliminary Report for PCT/JP2013/051448, dated Oct. 9, 2014.

Office Action, mailed Sep. 1, 2015, which issued during the prosecution of Japanese Patent Application No. 2014-507468, which corresponds to the present application.

* cited by examiner

CARRIAGE FOR ULTRASONIC DIAGNOSIS DEVICE

TECHNICAL FIELD

The present invention relates to a cart (carriage) configured to place a portable ultrasonic diagnostic apparatus thereon and used for moving, and in particular, it relates to the cart used specifically for an ultrasonic diagnostic apparatus, the cart having a high degree of flexibility in varying the position of a top board for placing the ultrasonic diagnostic apparatus thereon and improving the usability of the ultrasonic diagnostic apparatus, when used in a place other than a laboratory. The portable ultrasonic diagnostic apparatus indicates a small-sized and carriageable apparatus, and includes a notebook-size ultrasonic diagnostic apparatus, and the like.

BACKGROUND ART

An ultrasonic diagnostic apparatus is widely used as a medical image diagnostic apparatus, relatively simple and non-invasively applicable, and various types of portable ultrasonic diagnostic apparatus have been developed, being available not only in a laboratory within a hospital, but also in a patients room or out of hospital. By way of example, a notebook-size device is put into practical use, having a structure that couples a display panel with an operating panel at one end in an openable and closable manner, the display panel being configured to display an image, and the like, taken by the ultrasonic diagnostic apparatus, and the operating panel being configured to input instructions necessary for ultrasonic measurement.

In addition, there is also developed a cart used specifically for moving this kind of portable ultrasonic diagnostic apparatus to an examination site, together with accessories such as a probe. An examination is performed under the condition that the ultrasonic diagnostic apparatus is mounted on the cart. Therefore, in addition to the traveling performance in moving, the cart is required to have a function at the examination site, to arrange the ultrasonic diagnostic apparatus at a position that facilitates the examination. The most fundamental function is a mechanism to move the top board up and down, on which the ultrasonic diagnostic apparatus is mounted. Most of the carts currently used are provided with an up-and-down movement mechanism (e.g., Patent Document 1).

The Patent Document 2 describes a structure, which is not a cart, but the ultrasonic diagnostic apparatus itself is provided with a mechanism allowing the operating portion to be movable, up and down, back and forth, and in a rotational direction.

PRIOR ART DOCUMENT

Patent Document

Patent Document 1
Japanese Unexamined Patent Application Publication No. 2010-57886
Patent Document 2
Japanese Unexamined Patent Application Publication No. 2007-6968

DISCLOSURE OF THE INVENTION

Problem to be Solved by the Invention

In an examination site other than a laboratory, there are many spatial restrictions in a location where the cart is fixed and a position where an operator manipulates the ultrasonic diagnostic apparatus in that location. Under such restrictions, it is demanded to enhance the operability of the ultrasonic diagnostic apparatus that is mounted on the cart. In the cart provided with a conventional up-and-down movement mechanism, however, there is a limit in the degree of flexibility in the position of the ultrasonic diagnostic apparatus, and it is not possible to satisfy the demand above. In the technique as described in the Patent Document 2, the operating portion of the apparatus is allowed to move in the directions other than the up-and-down direction. However, the range of up-and-down movement and the range of rotation are limited to a certain extent, considering the relations with the display portion.

As for the case where the cart is movable up and down only, or only a part of the ultrasonic diagnostic apparatus is movable, it is not necessary to consider a relationship between the gravity point of the ultrasonic diagnostic apparatus and the moving mechanism. However, for the case where a mechanism is provided for moving the top board to place the ultrasonic diagnostic apparatus thereon, the relationship between the gravity point of the apparatus and the cart is significant.

An object of the present invention is to provide a cart for an ultrasonic diagnostic apparatus, the cart being high in the degree of flexibility in moving the top board on which the ultrasonic diagnostic apparatus is placed, and wherever it is moved, the posture of the ultrasonic diagnostic apparatus mounted on the top board never becomes unstable, achieving a stable operation.

Means to Solve the Problem

In order to solve the above problem, the cart for the ultrasonic diagnostic apparatus of the present invention is provided with a supporter for supporting a top board, the supporter having a vertical movement mechanism and a swing mechanism. The vertical movement mechanism is fixed on a base of the cart. A movable part of the vertical movement mechanism is provided with the swing mechanism that swings up and down, and this configuration allows the top board to move up and down according to both the vertical movement mechanism and the swing mechanism. A junction of the movable part on which the swing mechanism is fixed, is positioned in such a manner as displaced from the vertical axis of the vertical movement mechanism.

The cart for ultrasonic diagnostic apparatus of the present invention is further provided with a mechanism to rotate the top board and/or to move the top board horizontally. This rotation mechanism allows the top board to rotate 360 degrees in a horizontal plane.

Effect of the Invention

According to the present invention, it is possible to remarkably increase the up-and-down movable range of the top board and the ultrasonic diagnostic apparatus placed thereon.

BEST MODE FOR CARRYING OUT THE INVENTION

Figure 1:
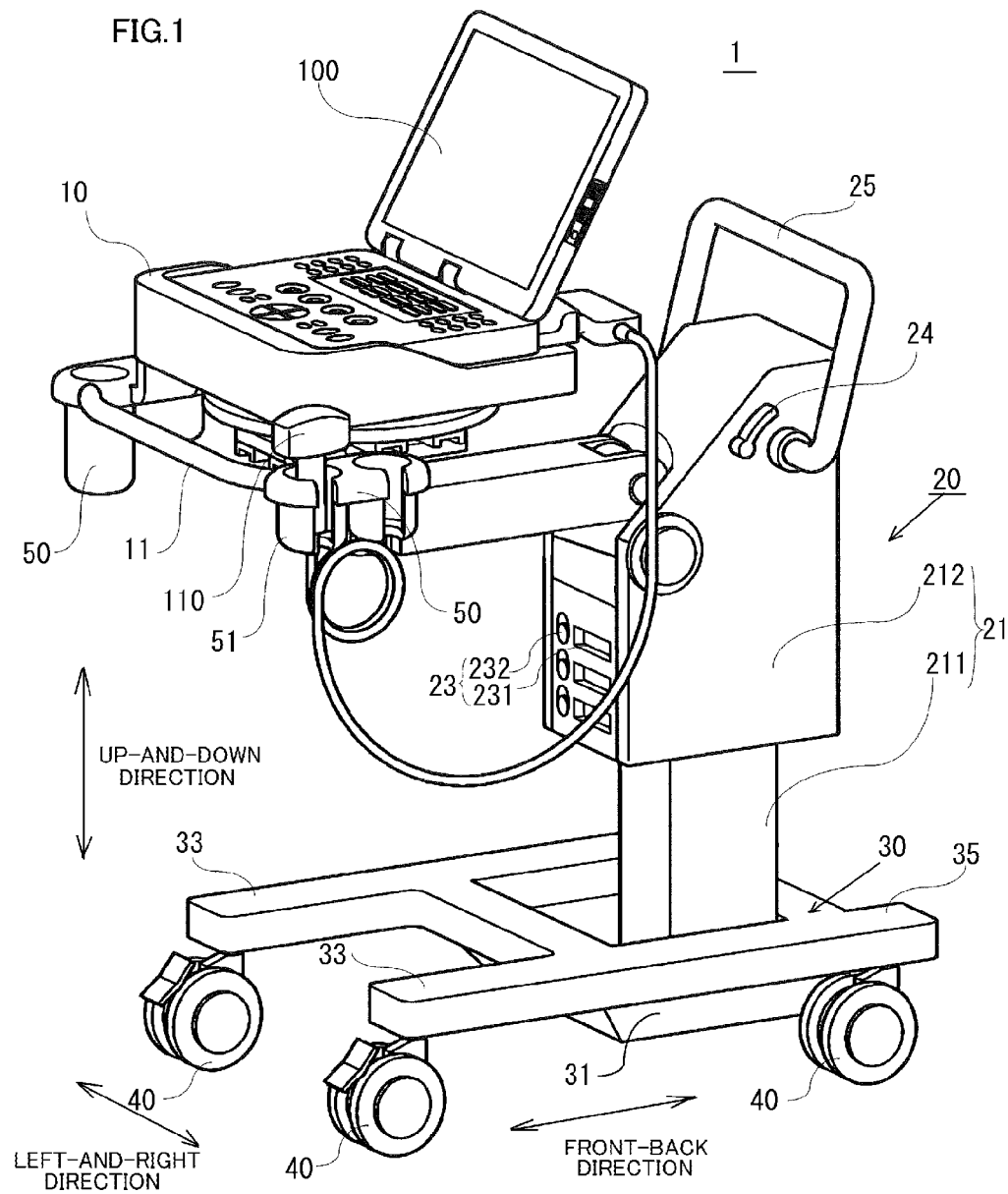
FIG. 1 is a perspective view illustrating one embodiment of the cart for the ultrasonic diagnostic apparatus of the present invention.
Figure 2:
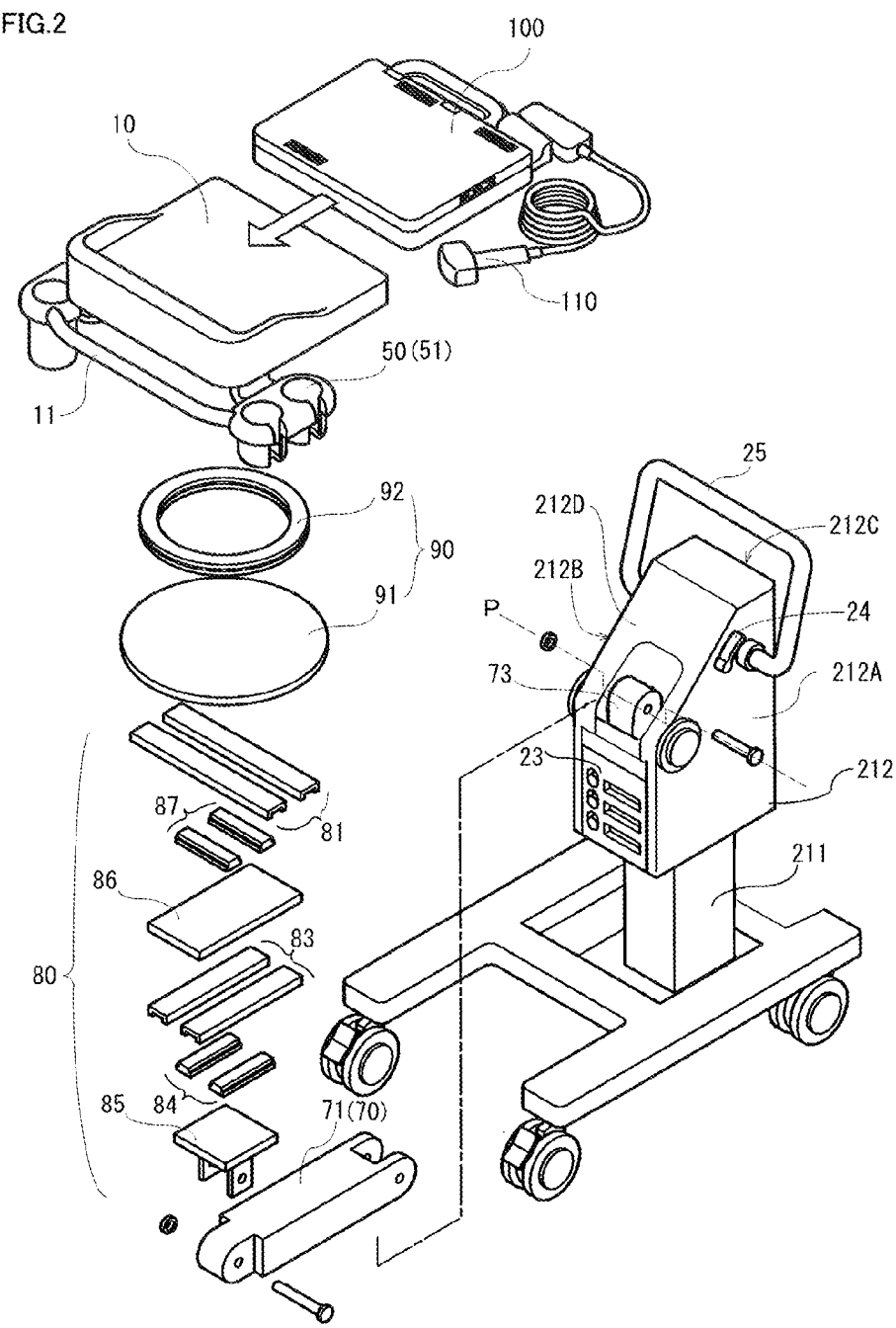
FIG. 2 is an exploded perspective view illustrating the structure of the cart for the ultrasonic diagnostic apparatus that is shown in FIG. 1.
Figure 3:
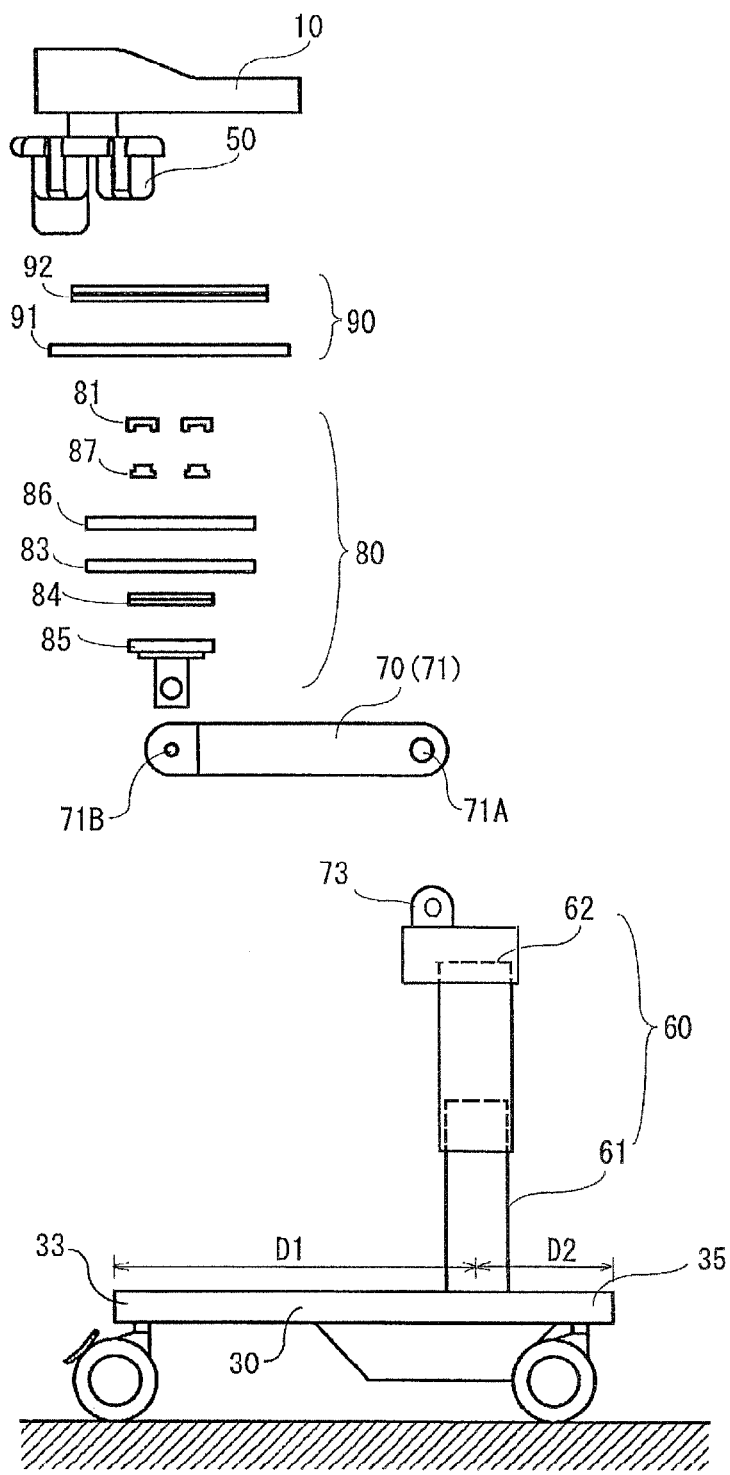
FIG. 3 is an exploded side view illustrating the structure of the cart for the ultrasonic diagnostic apparatus that is shown in FIG. 1.

Hereinafter, with reference to the accompanying drawings, a cart for an ultrasonic diagnostic apparatus (hereinafter, simply referred to as "cart") according to a preferred embodiment of the present invention will be explained. FIG. 1 illustrates an overall external view of the cart according to the embodiment of the present invention. FIG. 2 and FIG. 3 are an exploded perspective view and an exploded side view, respectively, illustrating each of the structural elements constituting the cart.

As illustrated, the cart 1 is made up of a top board 10 configured to place the ultrasonic diagnostic apparatus 100 thereon, a supporter 20 configured to support the top board 10, and a base 30 on which wheels 40 are fixed. The cart is used with placing the wheels 40 on a floor as shown in the figure, and the direction vertical to the floor surface is referred to as "height direction" or "up-and-down direction" in the following descriptions. Furthermore, the direction in which the cart 1 travels is referred to as "traveling direction" or "front-back direction", and the direction orthogonal thereto is referred to "left-and-right direction".

As illustrated in FIG. 2, the top board 10 is a member having an upper surface on which a concave shape is formed for accepting the underside of the operating panel of the notebook-size ultrasonic diagnostic apparatus 100, for instance, being thin in the height direction, and the back side is fixed on the rotation mechanism described below. The top board 10 is equipped with a probe holder 50 at an arbitrary position for placing therein a probe 110 for ultrasonic examination. The probe holder 50 may be fixed on the top board 10, or may be freely attachable and detachable. In the embodiment as illustrated, the probe holders 50 on which cups 51 are fixed for placing the probe therein, are mounted on both sides of the top board 10.

On the front end of the top board 10, there is provided an operating handle 11 for manipulating the top board 10. An operator holds this operating handle 11, allowing the top board 11 to rotate, or move forward, backward, left, or right as described below.

The supporter 20 is provided with plural mechanisms configured to move the top board 10, and a part or all of those mechanisms are covered by a cover 21 (211 and 212) that establishes integrity in design with the top board 10.

As a mechanisms for moving the top board 10, the cart of the present embodiment is provided with a vertical movement mechanism, a swing mechanism, a horizontal movement mechanism, and a rotation mechanism. Hereinafter, details of each of the mechanisms will be explained.

As illustrated in FIG. 3, the vertical movement mechanism 60 is made up of a fixed part 61 being fixed on the base 30, and a movable part 62 movable in the vertical direction with respect to the base 30. A publicly known multi-cylinder or single-cylinder damper (oil damper), or the like, may be utilized as the vertical movement mechanism made up of the fixed part 61 and the movable part 62. In other words, the fixed part 61 serves as the cylinder part of the damper, and the movable part 62 serves as the piston part, and the cylinder part is filled with fluid such as oil for controlling the up-and-down movement. The movable range (stroke) in the up-and-down direction of the vertical movement mechanism 60 is not particularly limited, but it is assumed as 300 mm in the present embodiment.

The movable part 62 is provided with a lock mechanism (not illustrated) configured to hold the movable part 62 at a desired position in the vertical direction. As the lock mechanism, a publicly known lock mechanism may be employed which is able to apply or release a lock, such an electromagnetic structure and a mechanical structure. The swing mechanism is coupled with the upper end of the movable part 62.

The fixed part 61 and the movable part 62 are respectively covered by the lower cover 211 and the upper cover 212, being independent of each other, and those parts are fixed to the covers respectively. The upper cover 212 is provided with a lever 24 configured to actuate or release the lock mechanism of the movable part 62. The outer shape of the upper cover 212 is larger than that of the lower cover 211, and it is structured in such a manner that when the movable part 62 goes down, the lower cover 211 covering the fixed part 61 goes into the upper cover 212.

The upper cover 212 is a housing having a bottom on which an opening is formed, the lower cover 211 being inserted into the opening, side surfaces 212A and 212B on both sides standing in the vertical direction from the bottom, and a back surface 212C connecting both of the side surfaces. The back surface 212C is a substantially vertical plane, and the width of both side surfaces becomes narrower in the front-back direction along with going upward from the bottom. This allows the shape of the front surface to be inclined, and the inclined front surface 212D continues to the upper surface.

On the front surface, there is formed a storage 23 for storing accessories such as an additional probe. The storage 23 is provided with plural connector parts 231 in a row arrangement each having the same shape as the connector for linking the probe-side connector, and release buttons for releasing the probe from the connector part are provided respectively for the connector parts. The swing mechanism 70 being coupled with the movable part 62 is located between both sides 212A and 212B in the upper part of the storage 23, and there is formed an opening on the front surface, the opening corresponding to a movable range of the swing mechanism.

An operating handle 25 is mounted on the upper cover 212. This operating handle 25 may be used as a handle for the operator to perform operations on the movable part 62 and an operation to move the cart. The vertical movement mechanism 60 may be operated by a pedal system, instead of using the operating handle. Though not illustrated, a power-supply unit is placed inside the cover.

As illustrated in FIG. 2 and FIG. 3, the swing mechanism 70 is made up of an arm-like member 71 being long relative to the diameter (hereinafter, referred to as "arm"), one end 71A in the longitudinal direction of the arm 71 is rotatably fixed on the upper end (a coupling member 73) of the movable part 62 in the up-and-down movement mechanism 60, in such a manner that the rotation axis P is parallel to the left-and-right direction of the cart. This configuration allows the arm 71 to rotate about the connection point with the coupling member 73, in a plane being orthogonal to the axis P. The rotation range is restrained by the shape of the upper end of the movable part 62 and the shape of the opening of the upper cover 212. In the present embodiment, it is rotatable by approximately 100 degrees, from the position where the longitudinal direction of the arm 71 is horizontal, to the position being inclined backward to some extent relative to the vertical direction.

The other end 71B of the arm 71 is coupled with the horizontal movement mechanism 80 and the rotation mechanism 90, via a coupling member 85. If the rotation of the arm 71 is assumed as the up-and-down movement on the other end 71B side, the movement corresponds to swing in the up-and-down direction. Therefore, in the present invention, this is referred to as the swing mechanism. The moving range in the up-and-down direction of the swing mechanism depends on the length and the rotation range of the arm 71. By combining the up-and-down movement of the swing mechanism 70 and the up-and-down movement of the aforementioned vertical movement mechanism 60, it is possible to expand the moving range in the up-and-down direction, and further, a degree of flexibility in the posture may be enhanced by optionally combining the two mechanisms for varying the position in the up-and-down direction.

The horizontal movement mechanism 80 is a structure to allow the top board 10 to move in the horizontal plane, and it may move in one dimensionally, or in two dimensionally. In the present embodiment, the structure allows two-way movement in the X-direction and Y-direction being orthogonal to each other, and it is made up of a combination of a pair of X-rails 81 (the first horizontal mechanism) and a pair of Y-rails 83 (the second horizontal mechanism).

Specifically, as illustrated in FIG. 2, on the upper surface of the coupling member 85 having the horizontal upper surface, being fixed on the end 71B of the arm 71 in the swing mechanism 70, there are fixed Y-sliders 84 that engage with the Y-rails 83 and slide along the Y-rails. The Y-rails 83 are fixed on a supporting plate 86, and X-sliders 87 are fixed on the surface (upper surface) of the supporting plate 86, opposite to the surface (lower surface) where the Y-rails 83 are fixed. The X-sliders 87 engage with the X-rails 81 and slide along the X-rails 81. The X-rails 81 are fixed on the undersurface of a circular plate constituting the rotation mechanism 90 described below, and the sliders 87 engage with the X-rails 81.

With this structure, the rotation mechanism 90 and the top board 10 thereon are movable in any of the direction along the X-rail 81 and the direction along the Y-rail 83. The moving range in the X-direction and the moving range in the Y-direction are not particularly limited, and they are not necessarily identical to each other. In order to accommodate the X-rails and the Y-rails in the projection area of the top board 10, it is preferable that the movement range is equal to or less than ±R, when the radius of the circle inscribing in the top board 10 (its principal plane) is assumed as R. In the present embodiment, as for the moving range of the Y-direction, considering that the moving amount in the Y-direction by the arm 71 of the swing mechanism 70 may be combined therewith, the moving range of the Y-direction is set to be smaller than the moving range in the X-direction. The moving range of the X-direction is a little smaller than ±½ of the width of the top board in the X-direction.

Figure 4:
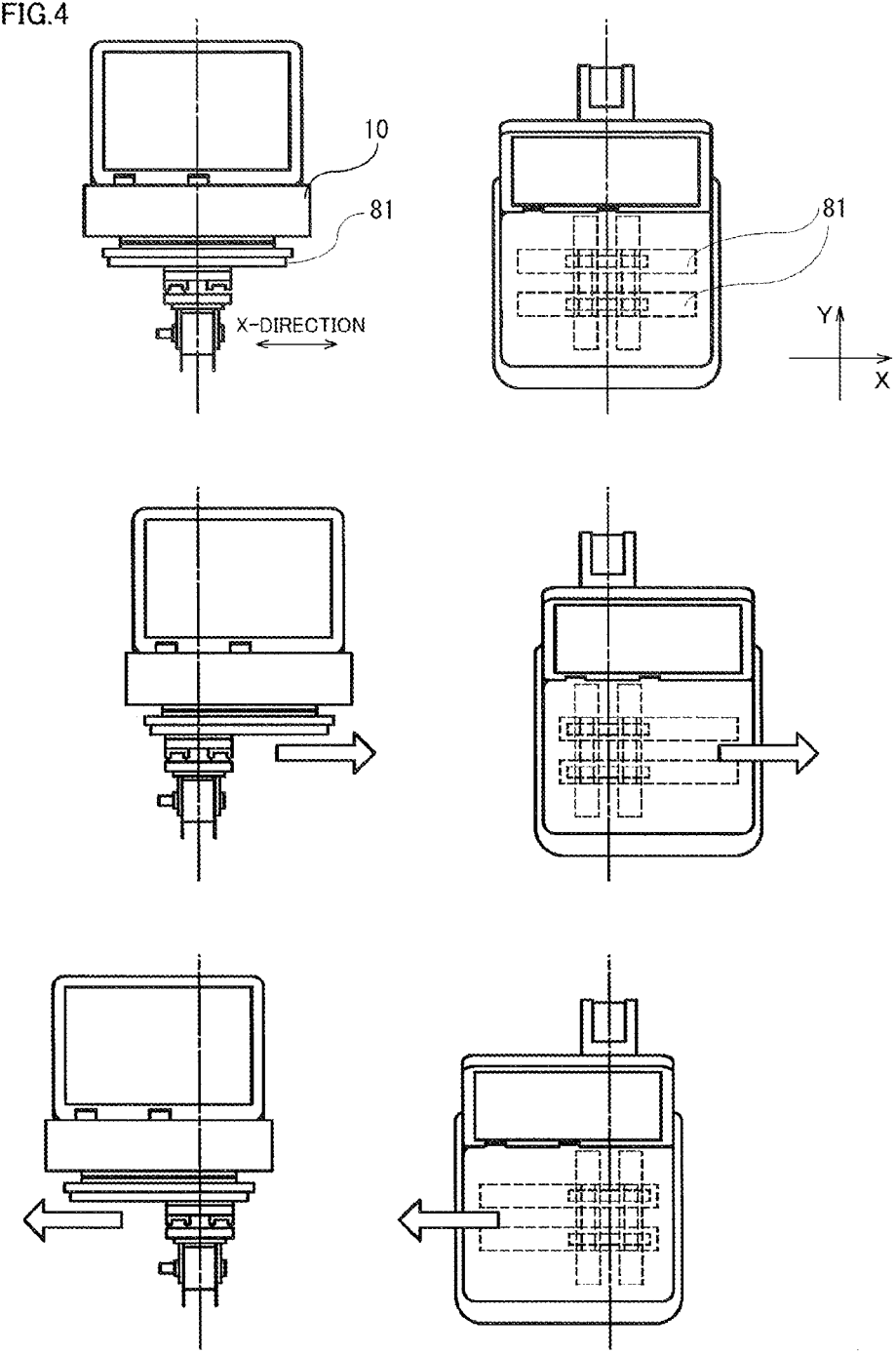
FIG. 4 illustrates X-direction movement of the top board according to a horizontal movement mechanism.
Figure 5:
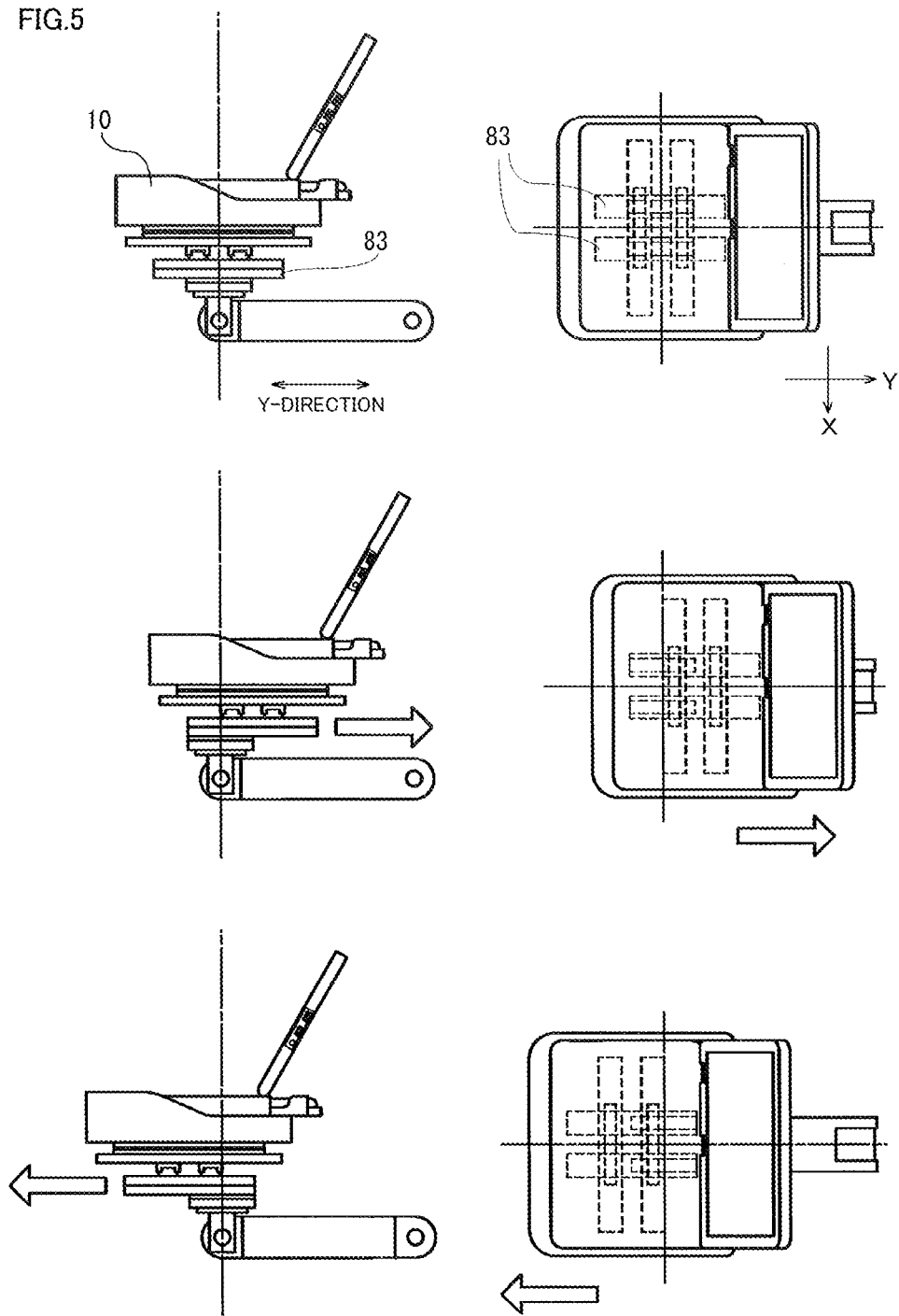
FIG. 5 illustrates Y-direction movement of the top board according to the horizontal movement mechanism.

FIG. 4 and FIG. 5 illustrate the way how the horizontal movement mechanism 80 moves the top board 10. FIG. 4 illustrates the front view (three illustrations on the left side) and the top view (three illustrations on the right side), showing the movement in the left-and-right direction. The two illustrations in the upper portion indicate that the center of the top board in the left-and-right direction coincides with the center of the X-rail 81 in the left-and-right direction, along the vertical direction. The two illustrations in the middle portion indicate the top board moves toward the right end from the above state, and the two illustrations in the lower portion indicate that the top board moves toward the left end. FIG. 5 illustrates the side view (three illustrations on the left side) and the top view (three illustrations on the right side), showing the movement in the front-back direction. It is illustrated here that the center of the top board in the front-back direction coincides with the center of the Y-rail 83 in the front-back direction, along the vertical direction (two illustrations in the upper portion). It is further illustrated that the top board moves to the rearmost position from the above state (two illustrations in the middle portion), and it moves to the frontend position (two illustrations in the lower portion). FIG. 4 and FIG. 5 illustrate the case where the direction of the X-rail (the X-direction) and the direction of the Y-rail (the Y-direction) respectively coincide with the left-and-right direction and the front-back direction of the cart. However, the aforementioned movements above are possible, also for the case where the rotation mechanism 90 turns the top board 10, and the X-direction does not agree with the left-and-right direction, and the Y-direction does not agree with the front-back direction.

The rotation mechanism 90 is a mechanism configured to support the top board 10 rotatably by 360 degrees, with respect to the aforementioned horizontal movement mechanism 80, and for this mechanism, a publicly known rotation mechanism may be employed, such as a mechanism made up of an axis and a bearing, and a mechanism employing a thrust ball bearing. As shown in FIG. 2, the rotation mechanism 90 of the present embodiment is made up of a circular plate 91 on which the X-rails 81 of the aforementioned horizontal movement mechanism 80 are fixed, a circular-shaped rail 92 fixed on the surface (upper surface) of the circular plate 91, opposite side of the surface (lower surface) on which the X-rails 81 are fixed, and plural convexes (not illustrated) on the backside of the top board 10, to be engaged with the circular shaped rail 92. As an alternative configuration, the circular shaped rail 92 may be fixed on the backside of the top board 10, and the plural convexes to be engaged with the rail 92 may be arranged vertically on the circular plate 91. In such a structure, the top board 10 is rotatable by 360 degrees in any rotating direction.

Figure 6:
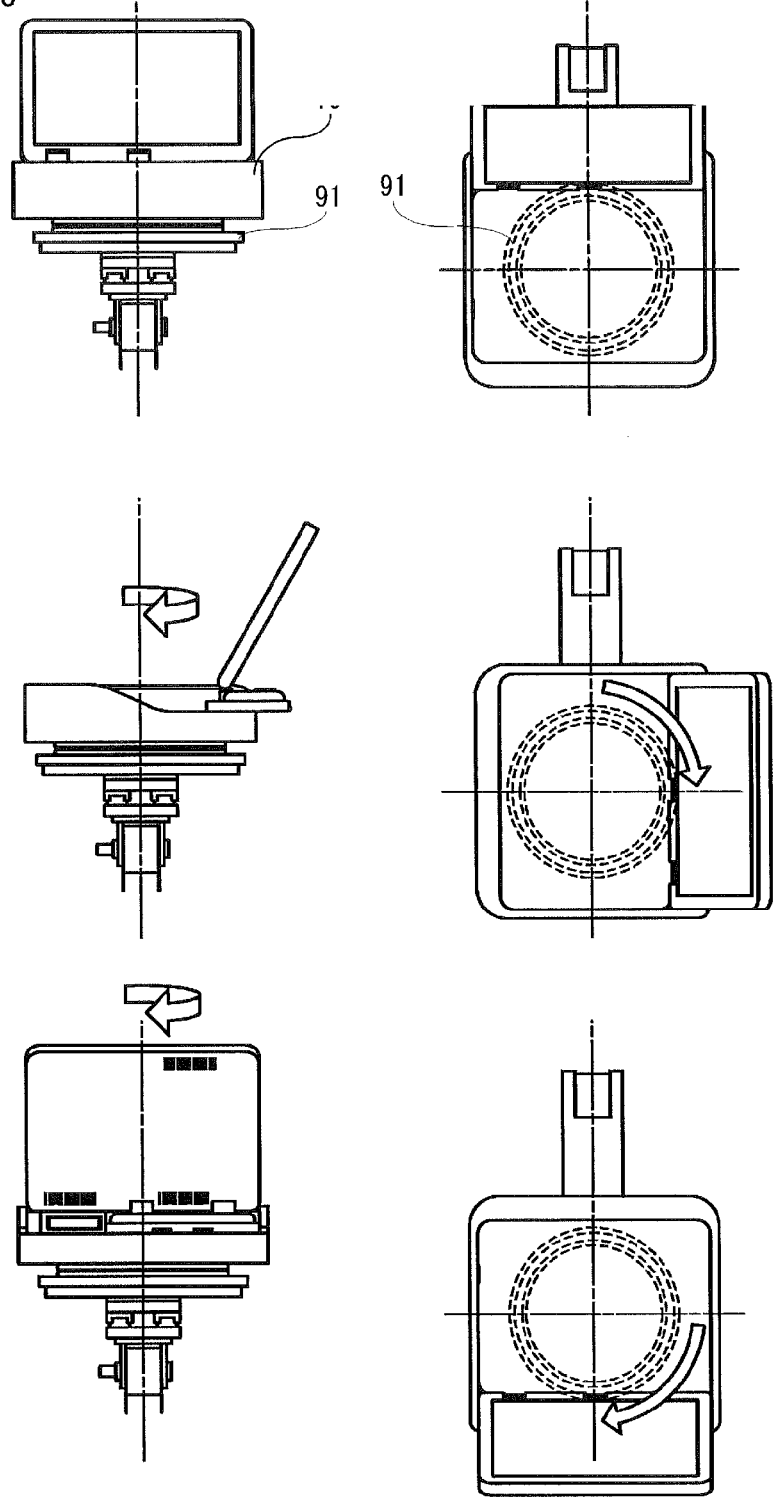
FIG. 6 illustrates the rotation of the top board according to the rotation mechanism.

FIG. 6 illustrates how the rotation mechanism 90 moves the top board 10. In the figure, the front view of the cart is shown in three illustrations on the left side, and the top view of the cart is shown in three illustrations on the right side. This figure indicates the rotating movement in the case where the center of the top board 10 coincides with the center of the X-rail and the Y-rail along the vertical direction. However, the rotation is possible at any positions as shown in FIG. 4 and FIG. 5, and even on a halfway position. As described above, by configuring the top board to be rotatable by 360 degrees in a horizontal plane, the operator is allowed to access the ultrasonic diagnostic apparatus placed on the top board from any position with respect to the cart. Therefore, this remarkably enhances the operability at the position with spatial restriction.

The vertical movement mechanism 60, the swing mechanism 70, the horizontal movement mechanism 80, and the rotation mechanism 90 as described above are basic movement mechanisms being provided in the supporter 20. In addition to those mechanical elements above, the supporter 20 may be provided with an optional structure or a structure for enhancing a design property, so far as it does not deteriorating the compact appearance.

Next, the base 30 will be explained. The base 30 supports the entire structure of the cart, allowing the cart to travel on the floor surface via the wheels 40, and it is made up of a main part 31 on which the fixed part 61 of the vertical movement mechanism 60 is fixed, legs 33 and 35 integrally provided on the main part 31, and the wheels 40 fixed on the legs 33 and 35. The main part 31 is a plate-like member, being integral with the lower cover 211 covering the fixed part 61 of the vertical movement mechanism 60 as a design, and four legs 33 and 35 extending nearly in the front-back direction are fixed on both sides of the fixed part 61 in the left-and right direction.

As shown in FIG. 3, as for the distance D1 and D2 of the legs 33 and 35, from the position where the fixed part 61 is fixed (the center thereof) respectively to the ends, the distance D1 to the forward leg 33 is longer than the distance D2 to the rearward leg 35. When an operator who is standing accesses the ultrasonic diagnostic apparatus on the top board 10, from the backside of the cart, while the top board 10 is positioned after turned by 180 degrees, above the vertical movement mechanism 60, the legs 35 being short on the rear side prevent the legs from protruding toward the operator side, relative to the position of the top board 1. This establishes preferable accessibility. The position where the fixed part 61 is fixed (the center thereof) is deviated rearward in the entire cart, and therefore, the center of gravity of the vertical movement mechanism 60 is also deviated rearward. Since the swing mechanism 70 is connected to the vertical movement mechanism 60 at the position forward relative to the center of the position where the fixed part 61 is fixed, this arrangement, together with the weight of the long forward legs 33, balances the deviation of the center of gravity of the vertical movement mechanism 60. This configuration allows stability of the posture as a whole to be maintained, even when the height of the top board varies.

The wheels 40 on at least either of the forward and the rearward legs 33 and 35 are provided with a revolving wheel shaft that enables traveling in variable directions. The wheel 40 may be provided with a stopper for halting the rotation (rotation around the wheel shaft).

Next, with reference to FIG. 7 to FIG. 10, operations and usage patterns of the cart according to the present embodiment having the aforementioned structures, will be explained.

Figure 7A:
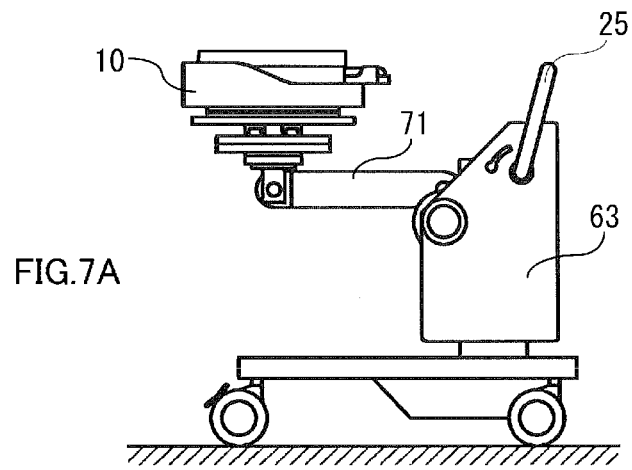
FIG. 7A and FIG. 7B illustrate examples of the postures of the cart upon travelling.
Figure 7B:
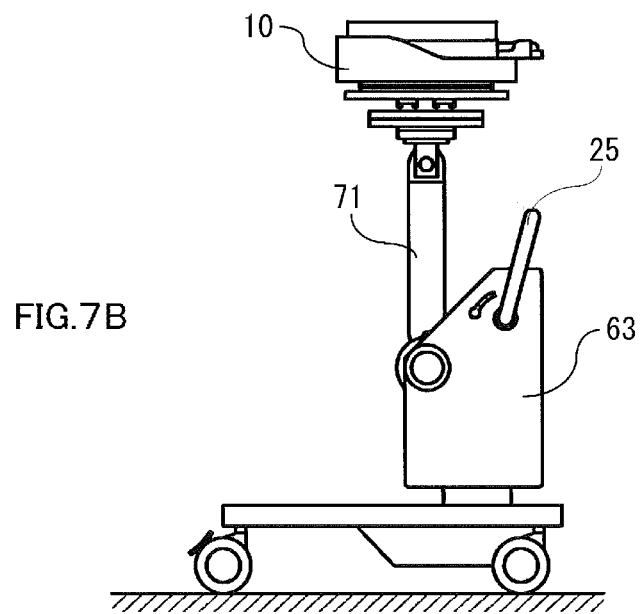

The ultrasonic diagnostic apparatus 100 is set on the top board 10 of the cart 1, and the operating handle 25 of the cart 1 is pushed to move the cart to a predetermined examination site. The posture of the top board 10 on this occasion is not limited. However, in order to enhance the forward visibility, the arm 71 is brought into a horizontal position as shown in FIG. 7A. In order to take a compact posture for traveling, the arm 71 is brought into an upright position as shown in FIG. 7B. In addition, the height of the movable part 63 of the vertical movement mechanism 60 is adjusted, so that the height of the operating handle 25 is brought into a position easily handled by the operator. Adjustment of the height of the movable part 63 is carried out by manipulating the operating handle 25 up and down. In this operation, the top board 10 simply moves up and down only along the vertical line.

Figure 8A:
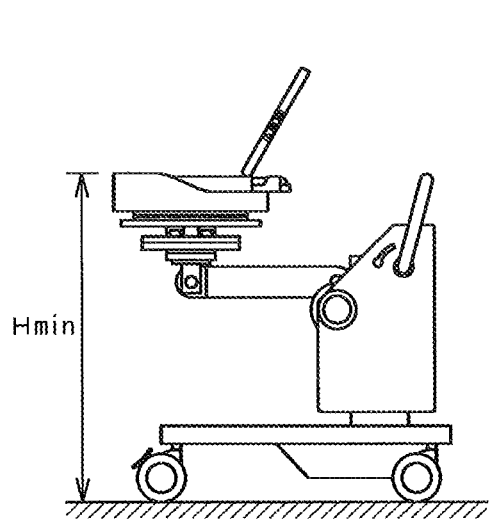
FIG. 8A to FIG. 8D illustrate the postures of the cart with the top board at the positions different in height, respectively.
Figure 8B:
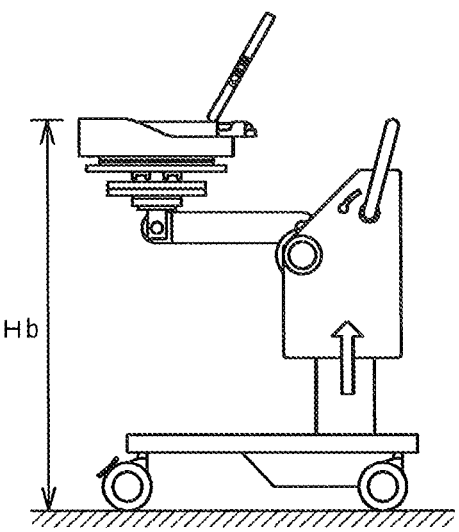
Figure 8C:
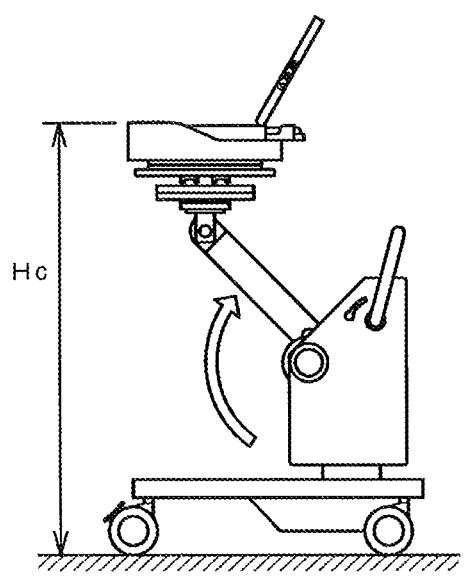

At the examination site, the examination is performed with varying the height, orientation, position of the top board 10 optionally, depending on the size and the shape of the space of the examination site. The height is adjusted by selecting the operation from the following as appropriate; the operation for moving the movable part 63 of the vertical movement mechanism 60 up and down (the operation by the operating handle 25), and the operation for moving the arm 71 of the swing mechanism 70 up and down (the operation by the operating handle 11). By way of example, when the operator performs the examination, while sitting on a chair with facing to the front side of the cart, the movable part 63 of the vertical movement mechanism 60 may be manipulated to get down the top board 10 until the lower limit height of the up-and-down moving range, and then, the swing mechanism 70 is manipulated so as to allow the top board 10 to go down until the lower limit Hmin of the height as shown in FIG. 8A. In the cart of the present embodiment, the lower limit of the operating panel surface of the ultrasonic diagnostic apparatus placed on the top board 10 is at the height of around 500 mm, and this enables examination at the low position such as examining lower extremity, and the like. As illustrated in FIG. 8B or FIG. 8C, the moving amount of the vertical movement mechanism 60 and the moving amount of the swing mechanism 70 are adjusted as appropriate, thereby establishing the height Hb or Hc, being suitable for any examination posture. By way of example, the height up to the operating panel surface may be changed to around 750 mm, as the height assumed as appropriate for the seated position.

At the position where the top board 10 is lowered by operating the swing mechanism 70 (FIG. 8A and FIG. 8B), the top board 10 extends out from the front surface of the cart. Here, by operating the horizontal movement mechanism 80, it is possible to adjust the position of the top board 10 in the front-back direction without changing the height. It is further possible to adjust the position in the left-and-right direction, if needed.

Figure 9:
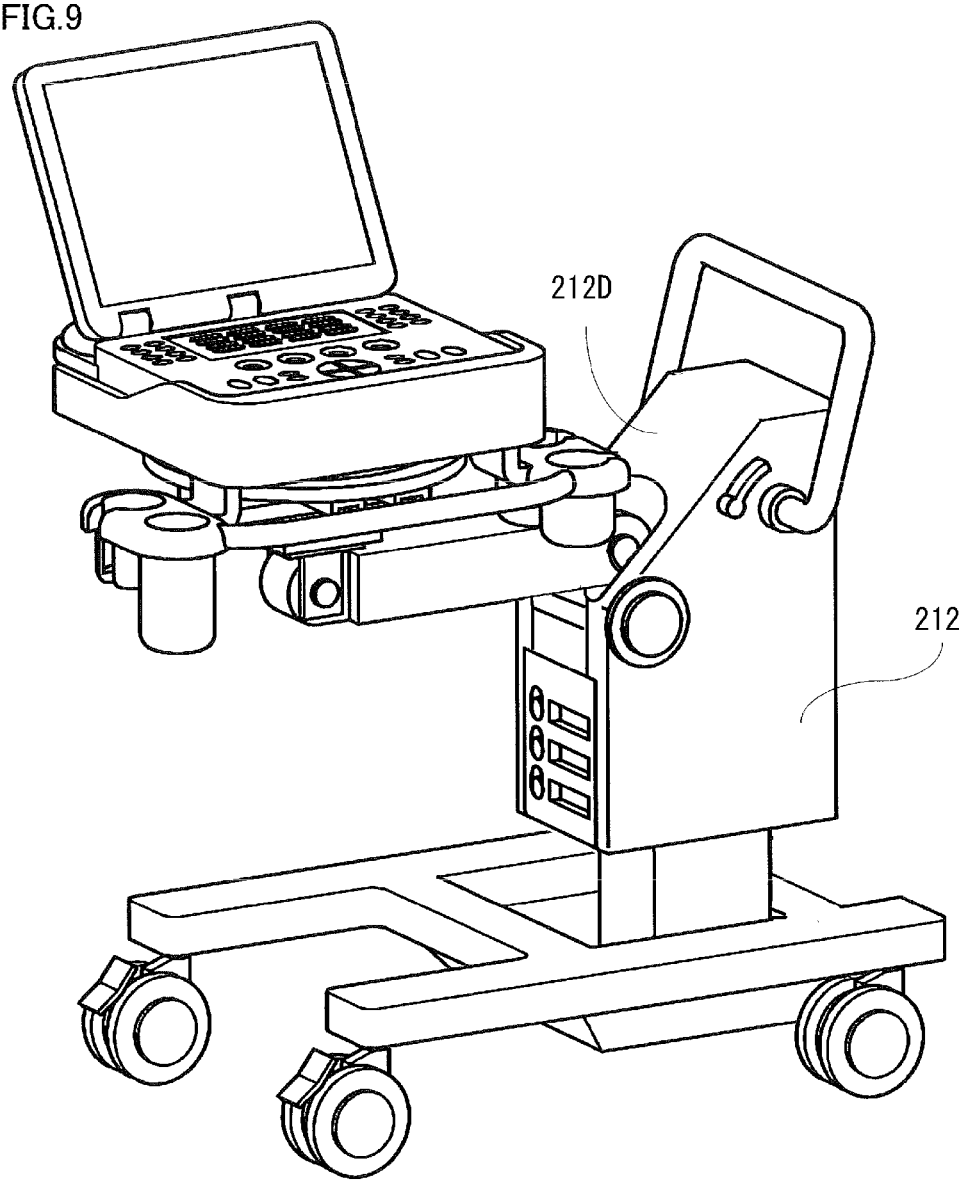
FIG. 9 is a perspective view illustrating one example of a posture suitable for performing an examination in the state of sitting on a chair.

Upon performing the operation in the seated position in the same manner as described above, in some cases, it is convenient for the operator to sit on the left side or on the right side of the cart, so as to perform the examination while facing to a patient, not facing to the front surface of the cart. In such a case, after the top board 10 is adjusted to be any height in the up-and-down direction, the handle 11 is manipulated to turn the rotation mechanism 90 to any direction and to any angle, thereby positioning the top board at the side of the cart as shown in FIG. 9. On this occasion, since the upper cover 212 has the front surface 212D being inclined, the top board 10 does not interfere with the upper cover 212 when rotating the top board 10, and this enables smooth rotation.

Figure 8D:
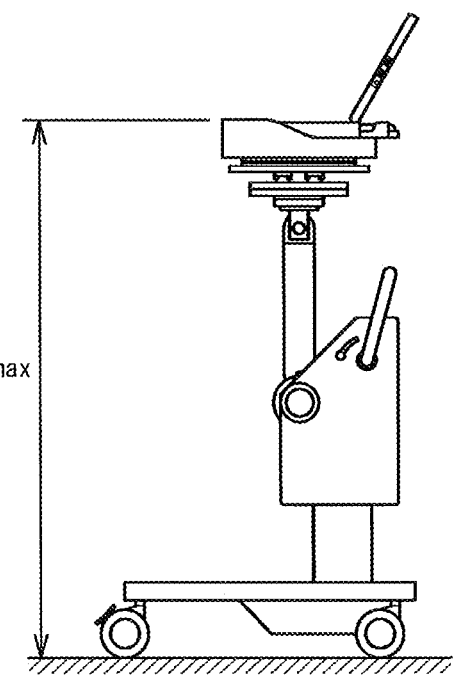
Figure 10:
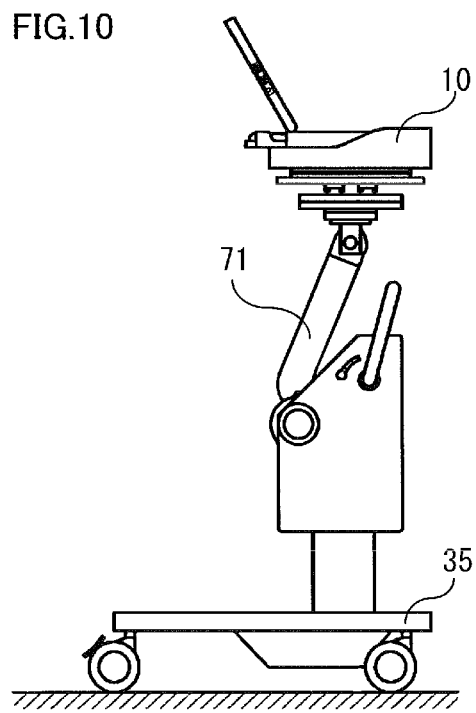
FIG. 10 is a side view illustrating one example of a posture suitable for performing an examination in the state of standing.

In the case where the examination is performed in the standing position, unlike the case of the seated position, after the top board 10 is adjusted to be the upper-limit height of the vertical movement mechanism 60, the handle 11 is manipulated so that the swing mechanism 70 allows the top board 10 to be positioned much higher (e.g., moved from the position of FIG. 8B to the position of FIG. 8D). The height Hmax of the operating panel of the ultrasonic diagnostic apparatus on the cart of the present embodiment is around 1,000 mm from the floor surface, in the state where the top board 10 is raised to the upper limit. In the standing position, operation from the backside of the cart is possible, and for this case, as shown in FIG. 10, for instance, the arm 71 of the swing mechanism 70 is inclined rearward from the vertical position, and further the top board 10 is rotated by 180 degrees. On this occasion, since the rearward leg 35 of the base 30 is located inner than the vertical surface on the front end of the top board 10, the operator is allowed to perform the examination without interference by the legs 35 with his or her motion.

Primary features of the cart for the ultrasonic diagnostic apparatus are as the following.

A combination of two mechanisms realizes any height and orientation of the top board 10 for placing the ultrasonic diagnostic apparatus 100 thereon. This configuration allows the moving range in the up-and-down direction to be expanded with a compact structure, facilitating the examination in the low position and in the standing position, and further allows the height to be adjusted so that it becomes suitable for the body height of the operator.

The two mechanisms for adjusting the up-and-down direction are made up of the vertical movement mechanism 60 for the vertical movement, and the swing mechanism 70 provided with the arm that swings about the upper end of the vertical mechanism, the upper end serving as the rotation center. Any of those two mechanisms are operable at any position in the height direction, bringing about high degree of flexibility in operation.

In addition to the two mechanisms to make adjustment in the up-and-down direction, the rotation mechanism 90 is also provided. Provision of the rotation mechanism allows the operator to access the ultrasonic diagnostic apparatus set on the top board from any direction, from the side surface or the back surface of the cart.

In addition to the two structures to make adjustment in the up-and-down direction, the horizontal movement mechanism 80 is further provided. The horizontal movement mechanism is made up of the mechanism for moving the top board in the left-and-right direction (the first horizontal mechanism 81) and, the mechanism for moving in the front-back direction (the second horizontal mechanism 83). The movement of the top board according to the swing mechanism causes the up-and-down movement to be accompanied with the movement in the front-back direction, and the horizontal movement mechanism is allowed to adjust the position in the front-back direction caused by this swing mechanism.

The vertical movement mechanism 60 is made up of the fixed part 61 and the movable part 63 respectively covered by the covers 211 and 212, being independent of each other. The cover 212 that covers the movable part 63 has the shape in which the front surface is inclined from the bottom surface toward the upper surface. With this configuration, wherever the top board is located in the height direction, the top board is allowed to rotate by the rotation mechanism, without causing interference between the cover and the top board.

The base 30 supporting the cart 1 is provided with the legs 33 and 35 on which the front wheels and the rear wheels are fixed, respectively, and the fixed part 61 of the vertical movement mechanism is arranged on the base in such a manner as being deviated toward the rear wheels side. The top board 10 is rotated above the upper cover that covers the movable part, and in the state where the front end of the top board is positioned on the rear side of the cart, the legs 35 on which the rear wheels are fixed are located inside the front end of the top board. This configuration allows the operator facing to the top board (the front end thereof) in the rear of the cart, to perform the actions such as examination, without interference by the rear wheels.

In the descriptions above, the embodiment of the cart for the ultrasonic diagnostic apparatus according to the present invention has been explained. However, the cart of the present invention is not limited to the embodiment as described above, and various modifications are possible. By way of example, in the present embodiment, the cart having both the horizontal movement mechanism and the rotation mechanism has been explained. However, the cart including only one of them, or the cart not having such structures are also included in the present invention. In the present embodiment, there is shown a configuration that the rotation mechanism is provided on the horizontal movement mechanism being coupled therewith. It is also possible to provide the horizontal movement mechanism on the rotation mechanism.

As the horizontal movement mechanism, the mechanism that is movable in two ways; the X-direction and the Y-direction, has been explained, but it may be movable only in one way, for example, in the front-back direction. The moving mechanism using the X-rail and the Y-rail has been explained, but another moving mechanism may be applicable, such as a combination of pinion and rack.

Each mechanism explained in the present embodiment is manually operated, but an electrically-operated mechanism may also be employed. Numeric values such as the moving range described in the above embodiment are just examples, and any modifications in design may be possible.

EXPLANATION OF REFERENCES

1 . . . CART, 10 . . . TOP BOARD, 11 . . . OPERATING HANDLE, 20 . . . SUPPORTER, 21 . . . COVER (211 . . . LOWER COVER, 212 . . . UPPER COVER), 30 . . . BASE, 33 . . . FORWARD LEG, 35 . . . REARWARD LEG, 40 . . . WHEEL, 50 . . . PROBE HOLDER, 60 . . . VERTICAL MOVEMENT MECHANISM, 61 . . . FIXED PART, 63 . . . MOVABLE PART, 70 . . . SWING MECHANISM, 71 . . . ARM, 80 . . . HORIZONTAL MOVEMENT MECHANISM, 81 . . . X-RAIL (FIRST HORIZONTAL MECHANISM), 83 . . . Y-RAIL (SECOND HORIZONTAL MECHANISM), 90 . . . ROTATION MECHANISM, 91 . . . CIRCULAR PLATE, 100 . . . ULTRASONIC DIAGNOSTIC APPARATUS

What is claimed is:

1. A cart for an ultrasonic diagnostic apparatus comprising,
   a top board configured to mount a portable ultrasonic diagnostic apparatus,
   a base being provided with wheels, and
   a supporter configured to link the top board with the base, wherein, the supporter comprising;
   a vertical movement mechanism having a movable part that is movable in a vertical direction with respect to the base, and
   a swing mechanism having a first end and a second end, the first end being coupled with the movable part of the vertical movement mechanism at a coupling point and the second end swinging with respect to the first end, the second end being coupled with the top board, wherein the coupling point of the movable part is displaced from a vertical line passing through the gravity center of the vertical movement mechanism, and wherein and the base has a first end and a second end, and a length to the first end from the center in a traveling direction at a position on which the vertical movement mechanism is fixed, is longer than a length to the second end from the center;

wherein the swing mechanism and vertical movement mechanism are configured to position the top board in a first posture where the swing mechanism is substantially horizontal with respect to the base and where the top board has a height suitable for examination while an operator is sitting and facing a front side of the cart, wherein the swing mechanism and vertical movement mechanism are configured to position the top board in a second posture where the swing mechanism is substantially vertical with respect to the base and where the top board has a height suitable for examination while the operator is standing and facing a back side of the cart, wherein the first end of the swing mechanism is rotatably fixed to the movable part and the second end of the swing mechanism is connected to the top board directly or indirectly, and wherein the movable part of the vertical movement mechanism is provided with a cover, and the cover is inclined from a second coupling point, where the swing mechanism is coupled with the movable part, toward an upper surface of the cover.

2. The cart for the ultrasonic diagnostic apparatus according to claim 1, further comprising,
a rotation mechanism between the swing mechanism and the top board, the rotation mechanism being configured to rotate the top board in a horizontal plane.

3. The cart for the ultrasonic diagnostic apparatus according to claim 1, further comprising,
a horizontal movement mechanism between the swing mechanism and the top board, the horizontal movement mechanism being configured to move the top board in a horizontal plane.

4. The cart for the ultrasonic diagnostic apparatus according to claim 3, wherein,
the horizontal movement mechanism comprises,
a first horizontal mechanism configured to move the top board in a first direction, and
a second horizontal mechanism configured to move the top board in a second direction intersecting with the first direction.

5. The cart for the ultrasonic diagnostic apparatus according to claim 1, wherein,
the base comprises a basal portion on which a fixed part of the vertical movement mechanism is fixed, wherein the wheels comprise at least two pairs of wheels being fixed on the basal portion.

6. The cart for the ultrasonic diagnostic apparatus according to claim 5, wherein,
a first pair of the two pairs of the wheels enables traveling in variable directions with respect to the traveling direction of the basal portion, and the first pair is mounted on the first end of the basal portion.

7. The cart for the ultrasonic diagnostic apparatus according to claim 5, wherein,
the basal portion has legs extending in the traveling direction, and the wheels are fixed on the legs.

8. The cart for the ultrasonic diagnostic apparatus according to claim 1, wherein,
the vertical movement mechanism comprises an operating handle adapted for a moving operation of the movable part and a traveling operation of the base.

9. A cart for an ultrasonic diagnostic apparatus comprising,
a top board configured to mount a portable ultrasonic diagnostic apparatus,
a base being provided with wheels, and
a supporter configured to link the top board with the base, wherein, the supporter comprising;
a vertical movement mechanism having a movable part that is movable in a vertical direction with respect to the base,
a swing mechanism having a first end and a second end, the first end being coupled with the movable part of the vertical movement mechanism at a coupling point and the second end swinging with respect to the first end, the second end being coupled with the top board, wherein the coupling point of the movable part is displaced from a vertical line passing through the gravity center of the vertical movement mechanism, and wherein and the base has a first end and a second end, and a length to the first end from the center in a traveling direction at a position on which the vertical movement mechanism is fixed, is longer than a length to the second end from the center, and
a horizontal movement mechanism between the swing mechanism and the top board, wherein the horizontal movement mechanism comprises a first horizontal mechanism configured to move the top board in a first horizontal direction, and a second horizontal mechanism configured to move the top board in a second horizontal direction intersecting with and perpendicular to the first direction.

\* \* \* \* \*